US010741942B2

(12) United States Patent
Sekido

(10) Patent No.: US 10,741,942 B2
(45) Date of Patent: Aug. 11, 2020

(54) CABLE MOUNTING STRUCTURE AND ENDOSCOPE

(71) Applicant: OLYMPUS CORPORATION, Tokyo (JP)

(72) Inventor: Takanori Sekido, Machida (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/555,441

(22) Filed: Aug. 29, 2019

(65) Prior Publication Data

US 2020/0084343 A1 Mar. 12, 2020

Related U.S. Application Data

(63) Continuation of application No. PCT/JP2017/008202, filed on Mar. 1, 2017.

(51) Int. Cl.
*H01R 12/53* (2011.01)
*A61B 1/00* (2006.01)
*A61B 1/05* (2006.01)
*H01R 4/70* (2006.01)
(Continued)

(52) U.S. Cl.
CPC .......... *H01R 12/53* (2013.01); *A61B 1/00114* (2013.01); *A61B 1/05* (2013.01); *H01R 4/70* (2013.01); *H01R 13/5221* (2013.01); *H04N 5/2251* (2013.01); *H04N 2005/2255* (2013.01)

(58) Field of Classification Search
CPC ............................. H01R 12/53; H01R 13/5221
See application file for complete search history.

(56) References Cited

U.S. PATENT DOCUMENTS 5,954,533 A * 9/1999 Hatagishi ............... H01R 43/24
439/397
6,268,561 B1 * 7/2001 Buscella ............... H01R 13/719
174/50.62
(Continued)

FOREIGN PATENT DOCUMENTS

JP       S60-005716 A      1/1985
JP       2005-168673 A     6/2005
(Continued)

OTHER PUBLICATIONS

1 International Search Report dated May 17, 2017 issued in International Application No. PCT/JP2017/008202.

*Primary Examiner* — James Harvey
(74) *Attorney, Agent, or Firm* — Scully, Scott, Murphy & Presser, P.C.

(57) ABSTRACT

A cable mounting structure includes: a clustered cable including at least two cables covered with an integration coat; a spacer configured to divide the at least two cables that are exposed by removing the integration coat at one end of the clustered cable into two groups and array the two groups of the cables along a upper surface and a lower surface of the spacer; a mounting board including a upper-side cable joint electrode to which a cable arrayed on the upper surface of the spacer is joined and a lower-side cable joint electrode to which a cable arrayed on the lower surface of the spacer is joined; and a resin seal in which a joint between the mounting board and the at least two cables and a mounting board side of the spacer is covered and sealed with a sealing resin.

8 Claims, 14 Drawing Sheets

(51) Int. Cl.
*H04N 5/225* (2006.01)
*H01R 13/52* (2006.01)

(56) References Cited

U.S. PATENT DOCUMENTS

| | | | | |
|---|---|---|---|---|
| 2005/0231343 | A1* | 10/2005 | Sinnett | H01R 13/58 340/442 |
| 2006/0191344 | A1* | 8/2006 | Hashimoto | A61B 8/00 73/632 |
| 2012/0146630 | A1* | 6/2012 | Itomi | G01D 5/145 324/207.25 |
| 2013/0244456 | A1* | 9/2013 | Sakamoto | A61B 1/00124 439/81 |
| 2013/0264107 | A1* | 10/2013 | Meyers | H05K 1/0218 174/268 |
| 2016/0367122 | A1 | 12/2016 | Ichimura et al. | |
| 2019/0069767 | A1* | 3/2019 | Mikami | A61B 1/005 |
| 2019/0296537 | A1* | 9/2019 | Mikami | A61B 1/00114 |
| 2020/0084343 | A1* | 3/2020 | Sekido | A61B 1/00114 |

FOREIGN PATENT DOCUMENTS

| | | |
|---|---|---|
| JP | 2006-223475 A | 8/2006 |
| WO | 2016/063603 A1 | 4/2016 |

\* cited by examiner

CABLE MOUNTING STRUCTURE AND ENDOSCOPE

CROSS-REFERENCE TO RELATED APPLICATION

This application is a continuation of PCT international application Ser. No. PCT/JP2017/008202, filed on Mar. 1, 2017 which designates the United States, incorporated herein by reference.

BACKGROUND

An endoscope that is inserted into a subject and observes a region to be examined has been known and is widely used in the medial field, etc. In an endoscope, a clustered cable that is a collection of a plurality of cables is used and is joined to a circuit board with the outer coating of the clustered cable being removed.

To prevent infection etc., endoscopes are sterilized before used again. In recent years, autoclave sterilization (high-pressure steam sterilization) has been employed as an easy and low-cost sterilization method. Autoclave sterilization has a risk of effect on electronic components. A technique to seal the area around electronic components, a mounting board, etc., with a sealing resin has been known (for example, refer to Japanese Laid-open Patent Publication No. 2005-168673).

According to Japanese Laid-open Patent Publication No. 2005-168673, filling, in addition to the area around a board on which electronic components are mounted and the area around joint of the board and cables, the outer circumference of a clustered cable and the space between cables with a sealing resin containing a moisture absorbing agent prevents steam from entering from the outside.

SUMMARY

A cable mounting structure according to the disclosure includes: a clustered cable including at least two cables covered with an integration coat; a spacer configured to divide the at least two cables that are exposed by removing the integration coat at one end of the clustered cable into two groups and array the two groups of the cables along a upper surface and a lower surface of the spacer; a mounting board including a upper-side cable joint electrode to which a cable arrayed on the upper surface of the spacer is joined and a lower-side cable joint electrode to which a cable arrayed on the lower surface of the spacer is joined; and a resin seal in which a joint between the mounting board and the at least two cables and a mounting board side of the spacer is covered and sealed with a sealing resin. An end face of the resin seal on a side of the clustered cable is positioned on a side of the mounting board with respect to an end of the spacer on a side of the clustered cable.

An endoscope according to the disclosure includes an insertion portion provided with an imaging device at a distal end of the insertion portion. The imaging device includes: an imaging element configured to generate an electric signal by receiving light and performing photoelectric conversion on the light; and the cable mounting structure. The imaging device is configured to perform image processing on the electric signal that is generated by the imaging element using the mounting board of the cable mounting structure.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
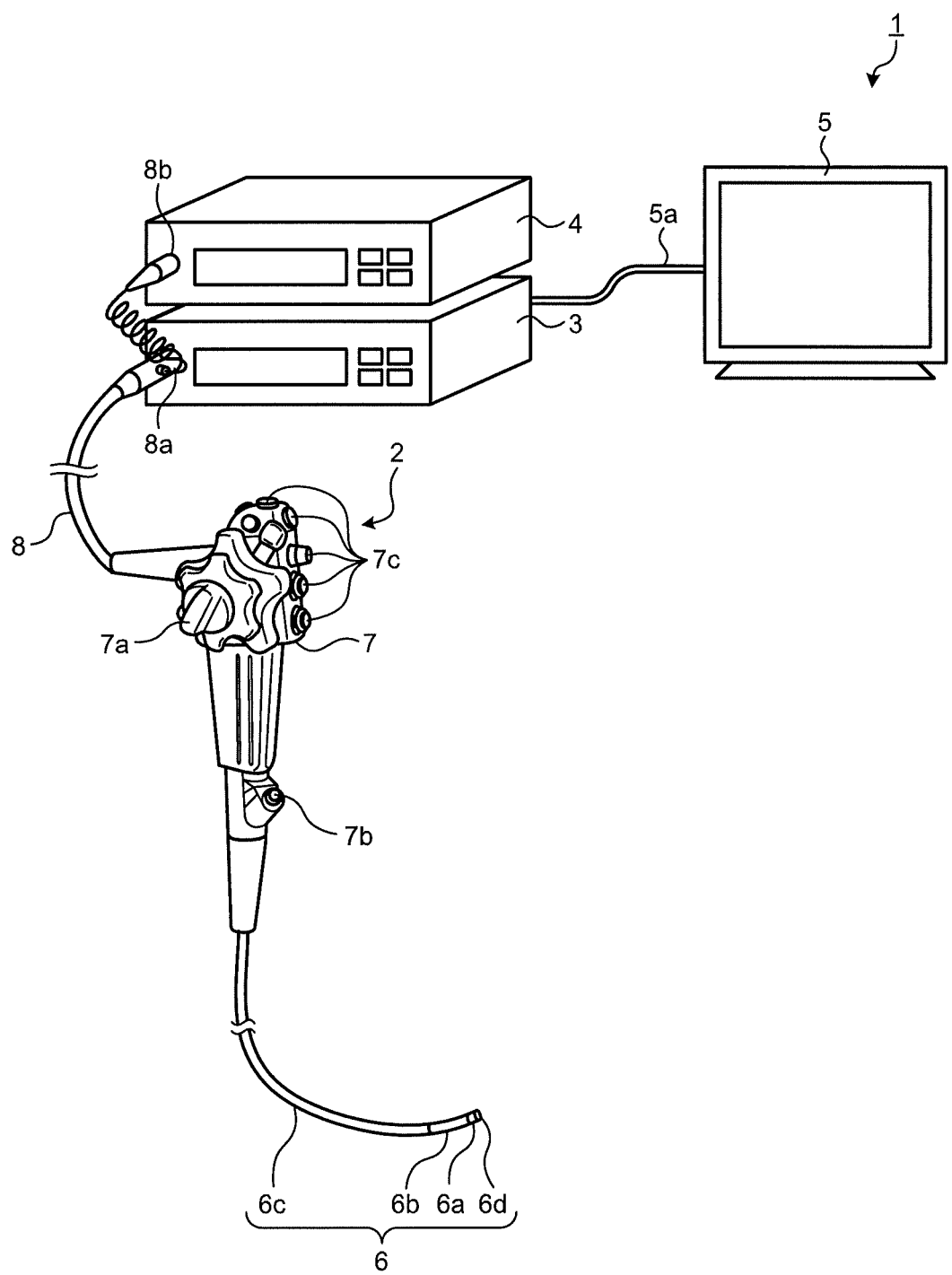
FIG. 1 is a diagram schematically illustrating an overall configuration of an endoscope system according to a first embodiment.

In the following description, an imaging device that includes a cable mounting structure and an endoscope system including the imaging device will be described as a mode for carrying out the disclosure ("embodiment" below) will be described below. The embodiments do not limit the disclosure. Like parts are denoted with like reference numbers in the drawings. The drawings are schematic and thus it should be noted that the relationship between thickness and width between members, the ratio between members, etc., differ from actual ones. The drawings contain parts whose sizes and ratio therebetween differ among the drawings.

First Embodiment

FIG. 1 is a diagram schematically illustrating an overall configuration of an endoscope system 1 according to a first embodiment of the disclosure. As illustrated in FIG. 1, the endoscope system 1 according to the first embodiment includes an endoscope 2 that is inserted into a subject, captures in-vivo images of the subject, and generates an in-vivo image signal; an information processing device 3 (an external processor) that performs given image processing on the signal of the images captured by the endoscope 2 and controls each unit of the endoscope system 1; a light source device 4 that generates illumination light of the endoscope 2; and a display device 5 that displays an image of the image signal on which the image processing has been performed by the information processing device 3.

The endoscope 2 includes an insertion portion 6 that is inserted into the subject; an operation unit 7 that is on the side of the proximal end of the insertion portion 6 and that is grasped by a practitioner; and a universal cord 8 that is flexible and that extends from the operation unit 7.

The insertion portion 6 is realized using an illumination fiber (light guide cable), an electronic cable, an optical fiber, etc. The insertion portion 6 includes a distal end part 6a that incorporates an imaging unit to be described below; a curve part 6b that is flexibly curved and that is formed of a plurality of curve pieces; and a flexible tube part 6c that has flexibility and that is provided on the side of the proximal end of the curve part 6b. In the distal end part 6a, an illuminator that illuminates the inside of the subject via an illumination lens, an observation unit that captures in-vivo images of the subject, an opening that communicates a treatment instrument channel, and an air-supply liquid-supply nozzle (not illustrated in the drawings) are provided.

The operation unit 7 includes a curve knob 7a that causes the curve part 6b in upward and downward directions and leftward and rightward directions; a treatment instrument insertion port 7b via which a treatment instrument, such as body forceps or a laser scalpel, is inserted into the body cavity of the subject; and a plurality of switches 7c to operate surrounding devices, such as the information processing device 3, the light source device 4, an air supply device, a water supply device, and a gas supply device. The treatment instrument that is inserted from the treatment instrument insertion port 7b gets out of an opening 6d at the distal end of the insertion portion 6 via a treatment instrument channel that is provided inside.

The universal cord 8 is formed using an illumination fiber, a cable, etc. The universal cord 8 divides at the proximal end and the end of one of the divided cords is a connector 8a and the end of the other part is a connector 8b. The connector 8a is detachable from the connector of the information processing device 3. The connector 8b is detachable from the light source device 4. The universal cord 8 transmits the illuminating light that is emitted from the light source device 4 to the distal end part 6a via the connector 8b and the illumination fiber. The universal cord 8 transmits the signal of the images captured by the imaging device to be described below to the information processing device 3 via the cable and the connector 8a.

The information processing device 3 performs the given image processing on the image signal that is output from the connector 8a and controls the overall endoscope system 1.

The light source device 4 is formed using a light source that emits light, a condenser lens, etc. Under the control of the information processing device 3, the light source device 4 emits light from the light source to supply, to the endoscope 2 that is connected via the connector 8b and the illumination fiber of the universal cord 8, the light as illumination light to the inside of the subject that is an object of which images are to be captured.

The display device 5 is formed using a displaying display using liquid crystals or organic electro luminescence (EL). The display device 5 displays various types of information containing images on which the given image processing is performed by the information processing device 3 via a video cable 5a. Accordingly, by operating the endoscope 2 while watching the images (in-vivo images) that are displayed by the display device 5, the practitioner is able to observe a desired site in the subject and determine the condition.

Figure 2:
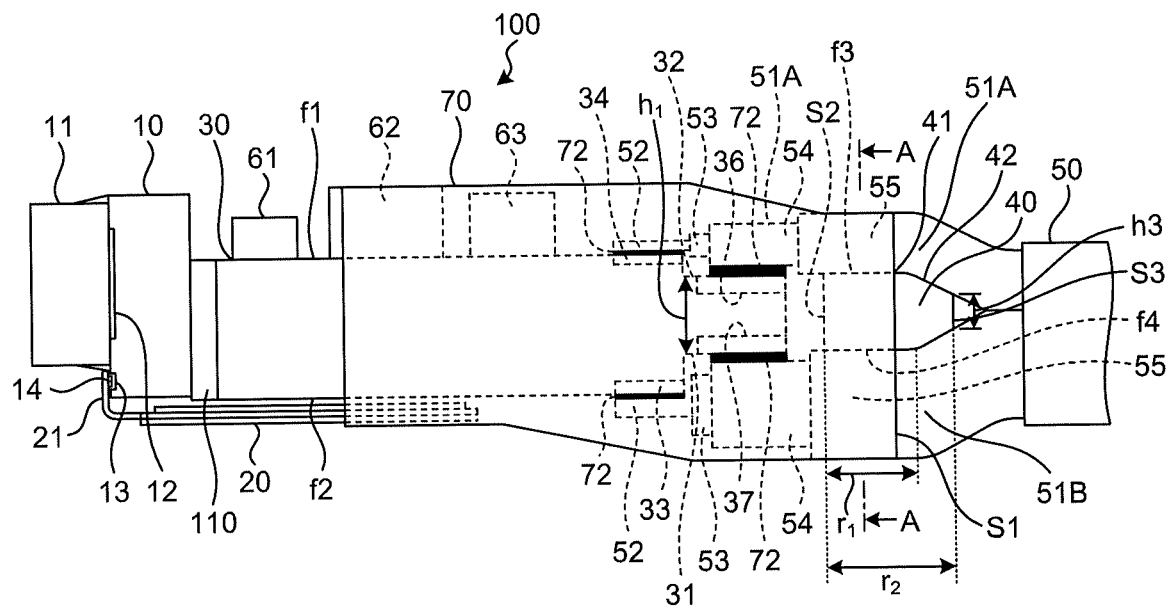
FIG. 2 is a side view of an imaging device that is used in the endoscope in FIG. 1.
Figure 3:
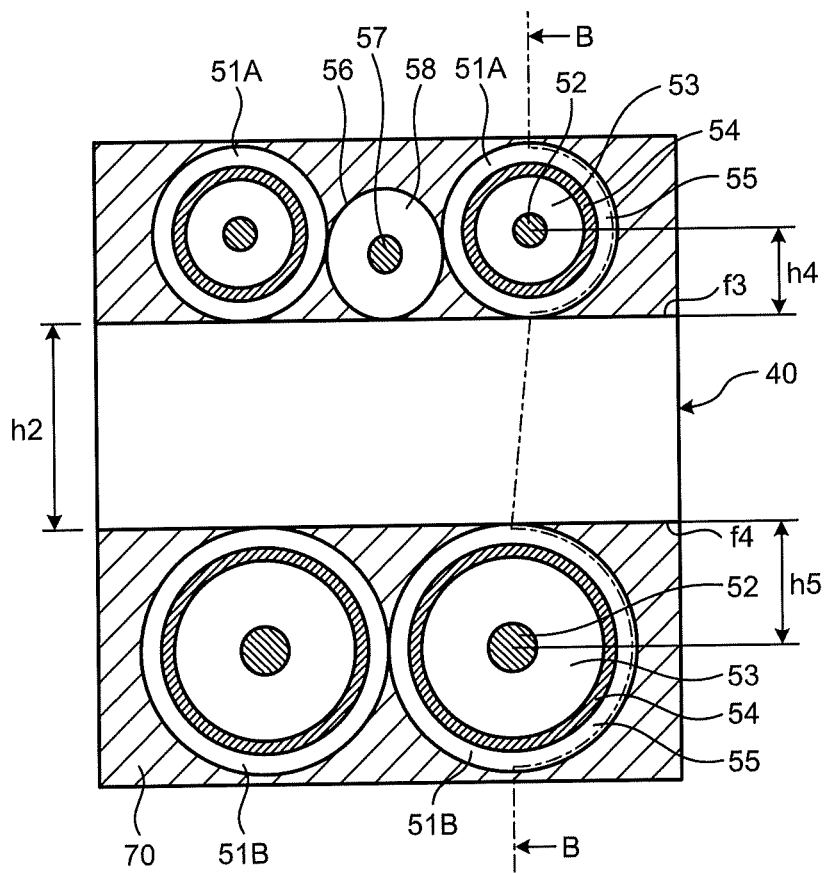
FIG. 3 is a cross-sectional view of the imaging device in FIG. 2 taken along the A-A line.

The configuration of the imaging device will be described in detail. FIG. 2 is a side view of an imaging device 100 that is used in the endoscope 2 in FIG. 1. FIG. 3 is a cross-sectional view of the imaging device 100 in FIG. 2 taken along the A-A line.

The imaging device 100 includes an imaging element 10, a flexible printed circuit board 20 ("FPC board 20" below), a mounting board 30, a spacer 40, and a clustered cable 50.

A cover glass 11 that protects a light receiver 12 is attached to the imaging element 10. The FPC board 20 is arranged such that the FPC board 20 extends from the imaging element 10 in a direction of optical axis and an inner lead 21 is joined to an electrode pad 13 of the imaging element 10 via a bump 14.

The mounting board 30 performs signal processing on an electronic signal that is generated by the imaging element 10 and a multilayer board forming an approximately rectangular shape is used as the mounting board 30. A first step 32 that is concave with respect to a reference surface that is a upper surface f1 of the mounting board 30 is formed in the upper surface f1 and a second step 31 that is concave with respect to a reference surface that is a lower surface f2 of the mounting board 30 is formed in the lower surface f2. For example, a board other than multilayer boards, such as a molded interconnect device (MID), may be used as the mounting board 30. Electronic components 61, 62 and 63 are mounted on the upper surface f1. In the upper surface f1, a core joint electrode 34 to which each of cores 52 and 57 of the clustered cable 50 to be described below is joined is formed and a shield cable joint electrode 36 to which each shield cable 54 is joined is formed on the first step 32 on a proximal end side. In the lower surface f2, a core joint electrode 33 to which each of the cores 52 and 57 of the clustered cable 50 is joined is formed and a shield cable joint electrode 37 to which each shield cable 54 is joined is formed on the second step 31 on the proximal end side. Herein, "the proximal end side" refers to "the side of the operation unit 7" and, for example, refers to the right side on the plane of FIG. 2.

In the mounting board 30, the first step 32 and the second step 31 are formed on the proximal end side to which the clustered cable 50 is joined to form the core joint electrode 34 and the shield cable joint electrode 36 at different levels, respectively, and form the core joint electrode 33 and the shield cable joint electrode 37 at different levels, respectively, so that the cables are joined to the mounting board 30 without being bent. This makes it possible to reduce a stress applied to the cable joint and thus inhibit joint failure, such as stripping. The imaging element 10 and the mounting board 30 are connected with a joint material 110, such as an adhesive.

The clustered cable 50 includes a simple cable 56, two coaxial cables 51A and two coaxial cables 51B that are two types of cables and the simple cable 56 and the coaxial cables 51A and 51B are covered with an integration coat that is removed at the end where the simple cable 56 and the coaxial cables 51A and 51B are thus drawn.

In the simple cable 56, the core 57 that is a conductor is covered with an insulative outer coat 58 and the outer coat 57 at the end is removed so that the core 56 is exposed.

Each of the coaxial cables 51A and 51B includes the core 52, an inner insulator 53 that covers the core 52, a shield cable 54 that is a conductor formed around the inner insulator 53, and an outer insulator 55 that covers the shield cable 54. Each of the ends of the coaxial cables 51A and 51B is removed to expose each of the core 52, the inner insulator 53, and the shield cable 54. The core 57 of the simple cable 56 and the cores 52 of the coaxial cables 51A are joined to the core joint electrode 34 using a conductive material, such as a solder 72, and the shield cables 54 of the coaxial cables 51A are joined to the shield cable joint electrode 36 by the solder 72, or the like. The cores 52 of the coaxial cables 51B are joined to the core joint electrode 33 using a conductive material, such as the solder 72, and the shield cables 54 of the coaxial cables 51B are joined to the shield cable joint electrode 37 using the solder 72, or the like.

The spacer 40 is arranged between two groups into which the simple cable 56 and the coaxial cables 51A and the coaxial cables 51B are divided, thereby arraying the simple cable 56 and the coaxial cables 51A and the coaxial cables 51B along an upper surface f3 and a lower surface f4, respectively. The simple cable 56 and the coaxial cables 51A are arrayed along the upper surface f3 and the coaxial cables 51B are arrayed along the lower surface f4.

The spacer 40 includes a cable arrangement part 41 in which the distance between the upper surface f3 and the lower surface f4 is uniform, that is, the spacer 40 forms a rectangular shape in a cross-sectional view taken along the A-A line, and a slope 42 that has a tapered shape where the distance between the upper surface f3 and the lower surface f4 gradually reduces from the side of the mounting board 30 toward the side of the clustered cable 50 and that is formed integrally with the cable arrangement part 41 on the side of the clustered cable 50. A surface S3 of the slope 42 on the rear end side is inserted to the vicinity of the part of the clustered cable 50 where the integration coat is removed. The spacer 40 is formed by shaping resin. The cable arrangement part 41 is not limited to a rectangular shape as long as the distance between the upper surface f3 and the lower surface f4 is uniform.

Providing the slope 42 on the proximal end side in the spacer 40 reduces a stress load to the bended part of the simple cable 56 and the coaxial cables 51A and 51B and arranging the simple cable 56 and the coaxial cables 51A and 51B in the cable arrangement part 41 having the upper surface f3 and the lower surface f4 that are flat makes it easy to hold the cable. Setting a height h2 of the cable arrangement part 41 of the spacer 40 substantially equal to a thickness h1 of the mounting board 30 on the proximal end side simplifies an operation of adjusting the heights of the cable and the mounting board and makes it easy to join the cable to the mounting board 30. When the height h2 of the cable arrangement part 41 of the spacer 40 is substantially equal to the thickness h1 of the mounting board 30 on the proximal end side, the height h2 is at or above a value obtained by subtracting the thickness of the outer insulator 55 from the height h1 and is at or under the thickness h1.

A resin seal 70 covers and seals the joint of the mounting board 30, the simple cable 56 and the coaxial cables 51A and 51B and the spacer 40, the simple cable 56, and the coaxial cables 51A and 51B with a sealing resin. The resin seal 70 also seals the electronic components 62 and 63. According to FIG. 2, the electronic component 61 is not sealed with the resin seal 70 but is sealed with resin as the electronic components 62 and 63 are sealed. It suffices if the resin seal 70 is formed such that a surface S1 on the proximal end side is at least positioned on the side of the clustered cable 50 with respect to a surface S2 of the spacer 40 on the side of the mounting board 30. Note that, by covering a half of a length r1 of the cable arrangement part 41 of the spacer 40 or more, the resin seal 70 is able to fix the simple cable 56 and the coaxial cables 51A and 51B together with the spacer 40 and attenuate the stress load on the joint between the cable and the mounting board 30.

In the first embodiment, the spacer 40 is arranged between two groups into which the simple cable 56 and the coaxial cables 51A and the coaxial cables 51B are divided and this makes it possible to prevent the sealing resin to enter the space between the cables that are divided vertically and inhibit an increase in rigid length of the imaging device 100. In order to prevent the sealing resin from entering the space between cables, it is preferable that the surface S1 of the resin seal 70 on the proximal end side be formed such that the surface S1 is positioned on the side of the mounting board 30 (front side) with respect to the surface S3 of the spacer 40 on the rear end side. A thickness h3 of the spacer 40 on the side of the proximal end of the cable is preferably designed to be larger than gaps h4 and h5 each between the center of the cable and the spacer 40. A liquid sealing resin has properties of permeating to a side with a small gap because of capillarity and thus an effect that the sealing resin tends to permeate to the center of the cable positioned on the side of the distal end of the cable and the side of the gaps h4 and h5 of the spacer 40 with a gap smaller in size than the gap occurring on the proximal end side of the cable of the spacer 40 (approximately equal to h3) is obtained, which is more desirable because the sealing resin is easily prevented from flowing out to the proximal end side of the cable.

Figure 4:
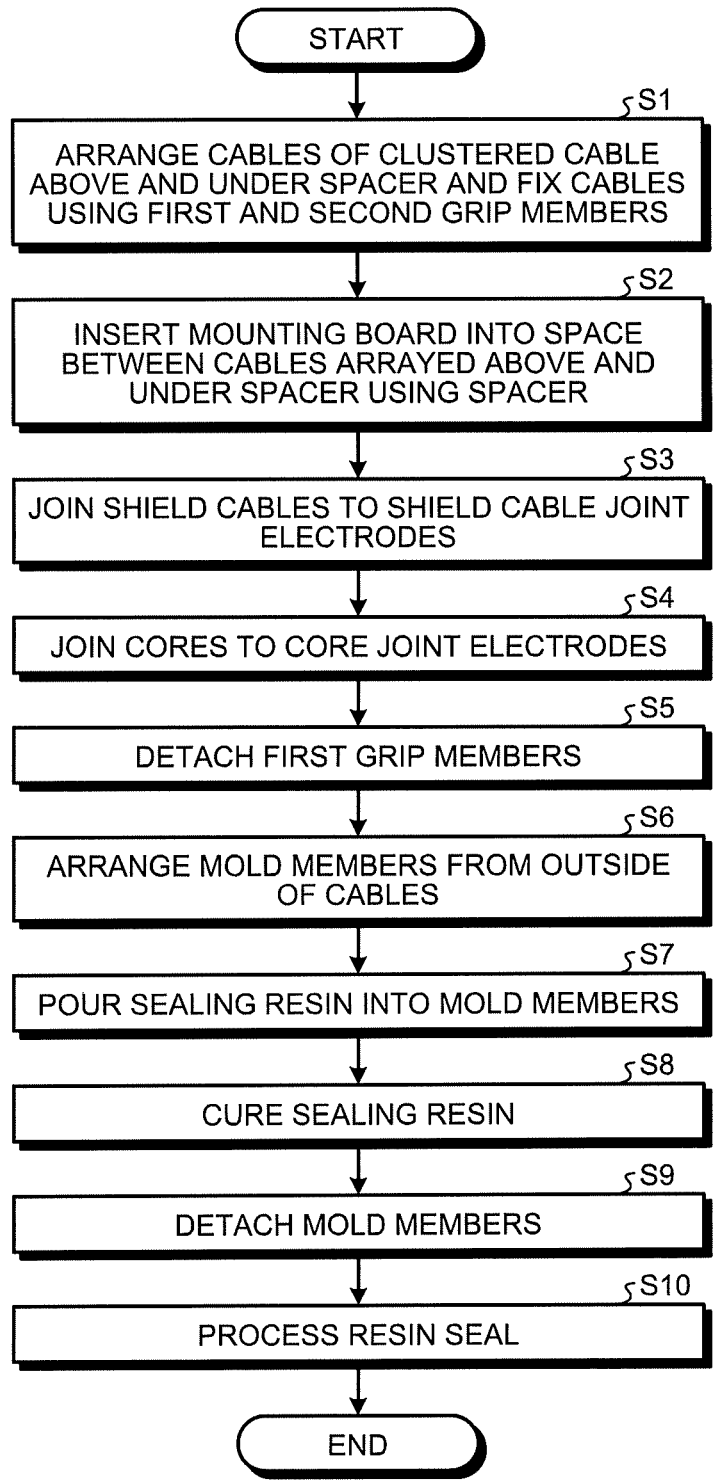
FIG. 4 is a flowchart illustrating a process of manufacturing an imaging device according to the first embodiment.

A method of manufacturing the imaging device 100 according to the first embodiment will be described with reference to the drawings. FIG. 4 is a flowchart illustrating a process of manufacturing the imaging device 100 according to the first embodiment. FIGS. 5 to 11 are diagrams illustrating the process of manufacturing the imaging device 100 according to the first embodiment. FIGS. 5, 6, 8, 9 and 10 are cross-sectional views taken along the B-B line in represented in FIG. 3 where the coaxial cables 51A and 51B are described not in cross-sectional views but in side views.

Figure 5:
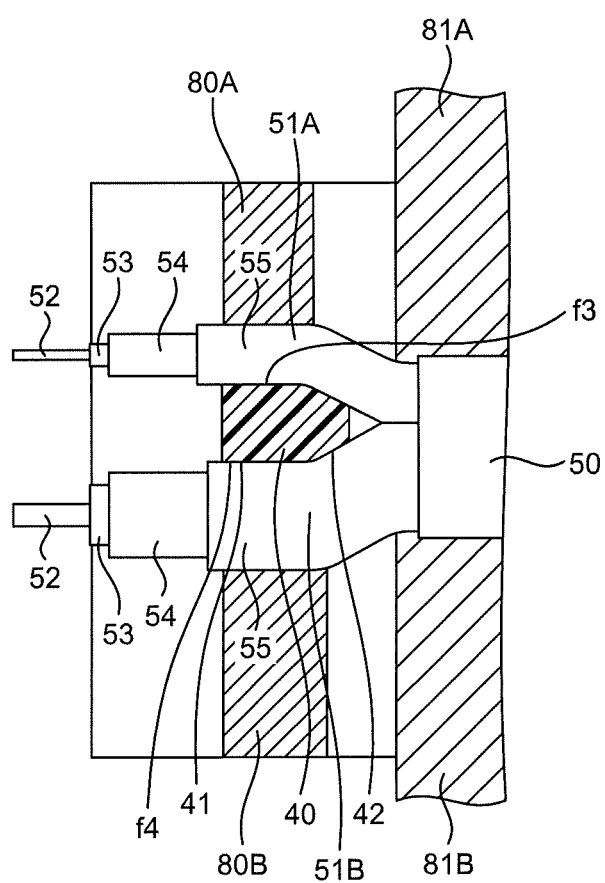
FIG. 5 is a diagram illustrating the process of manufacturing an imaging device according to the first embodiment.

First of all, as illustrated in FIG. 5, an integration coat at the end of the clustered cable 50 is removed, the simple cable 56 and the coaxial cables 51A are arrayed on the upper surface f3 of the spacer 40, the coaxial cables 51B are arrayed on the lower surface f4 and, and then the spacer 40 and the simple cable 56 and the coaxial cables 51A and 51B, which are arrayed, are fixed using first grip members 80A and 80B and second grip members 81A and 81B. The spacer 40 and the simple cable 56 and the coaxial cables 51A and 51B, which are arrayed, are fixed using the first grip members 80A and 80B and the clustered cable 50 is fixed using the second grip members 81A and 81B (step S1). The spacer 40 is interposed between the simple cable 56 and the coaxial cables 51A and the coaxial cables 51B and thus is fixed indirectly by the first grip members 80A and 80B.

Figure 6:
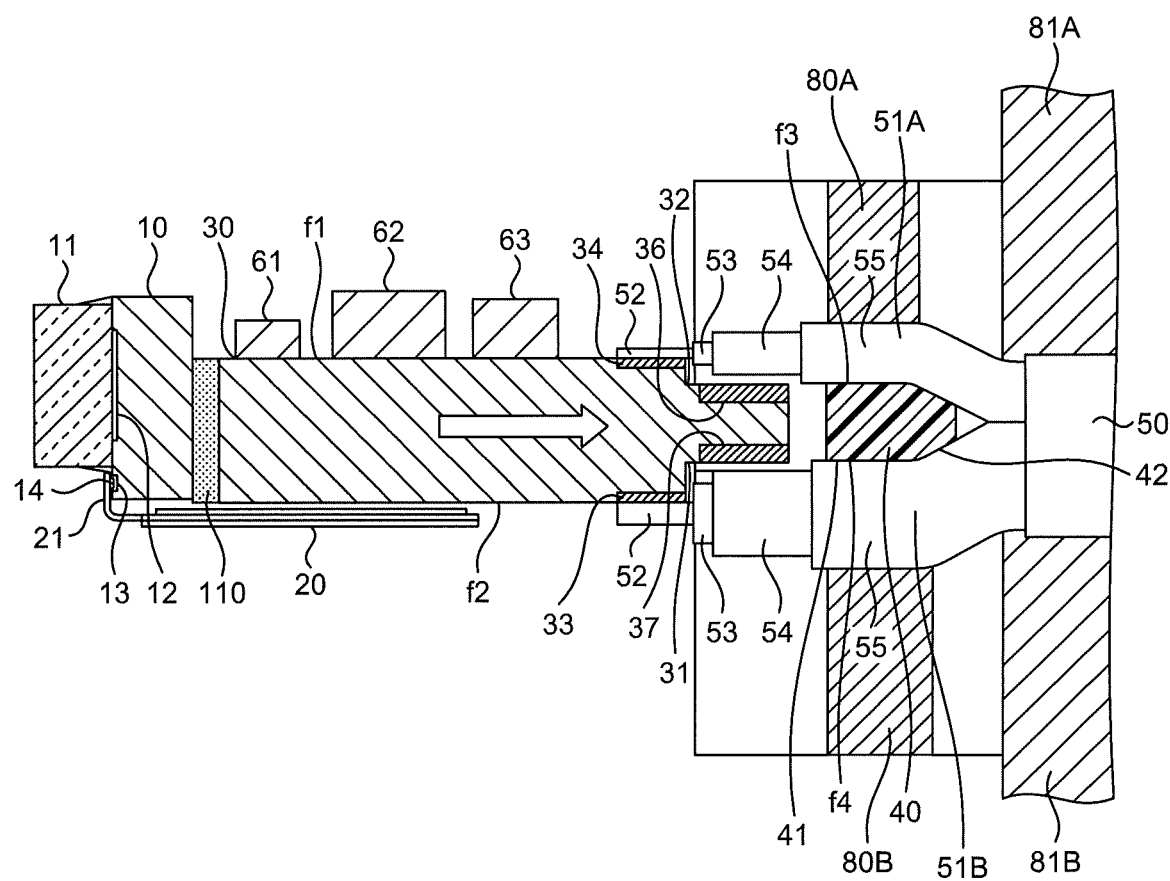
FIG. 6 is a diagram illustrating the process of manufacturing an imaging device according to the first embodiment.

As illustrated in FIG. 6, the mounting board 30 is inserted into the space between the simple cable 56 and the coaxial cables 51A and the coaxial cables 51B that are arranged on the upper surface f3 and the lower surface f4 of the spacer 40, respectively (step S2). The mounting board 30 is inserted to a position such that the core joint electrodes 34 and 33 are below the cores 52 and 57.

Figure 7:
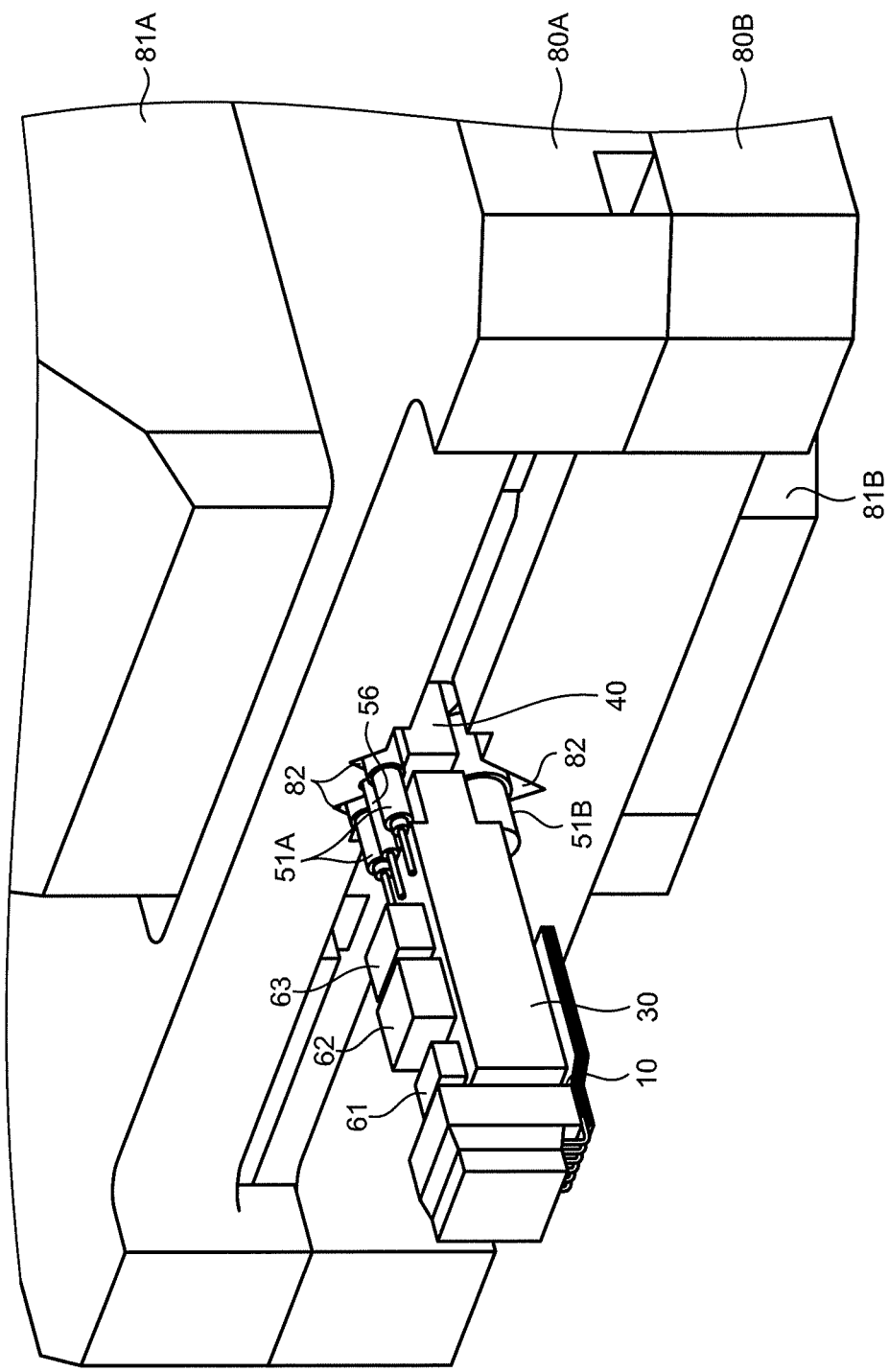
FIG. 7 is a diagram illustrating the process of manufacturing an imaging device according to the first embodiment.

FIG. 7 is a perspective view from the side of the first grip members 80A and 80B after step S2. In the first grip members 80A and 80B, grooves 82 that prevent the simple cable 56 and the coaxial cables 51A and 51B that are arrayed on the upper surface f3 and the lower surface f4 of the spacer 40 from shifting are formed.

The mounting board 30 is inserted into the space between the simple cable 56 and the coaxial cables 51A and the coaxial cables 51B (step S2) and the shield cables 54 of the coaxial cables 51A and 51B are joined to the shield cable joint electrode 36 or the shield cable joint electrode 37 with the solder 72 (step S3) and then the core 56 of the simple cable 56 and the cores 52 of the coaxial cables 51A and 51B are joined to the core joint electrode 34 or the core joint electrode 33 (step S4). Joining the shield cable 54 first enables the spacer 40 to be interposed between the simple cable 56 and the coaxial cables 51A and 51B and to be fixed and thus enables reduction in shifting of the spacer 40.

Figure 8:
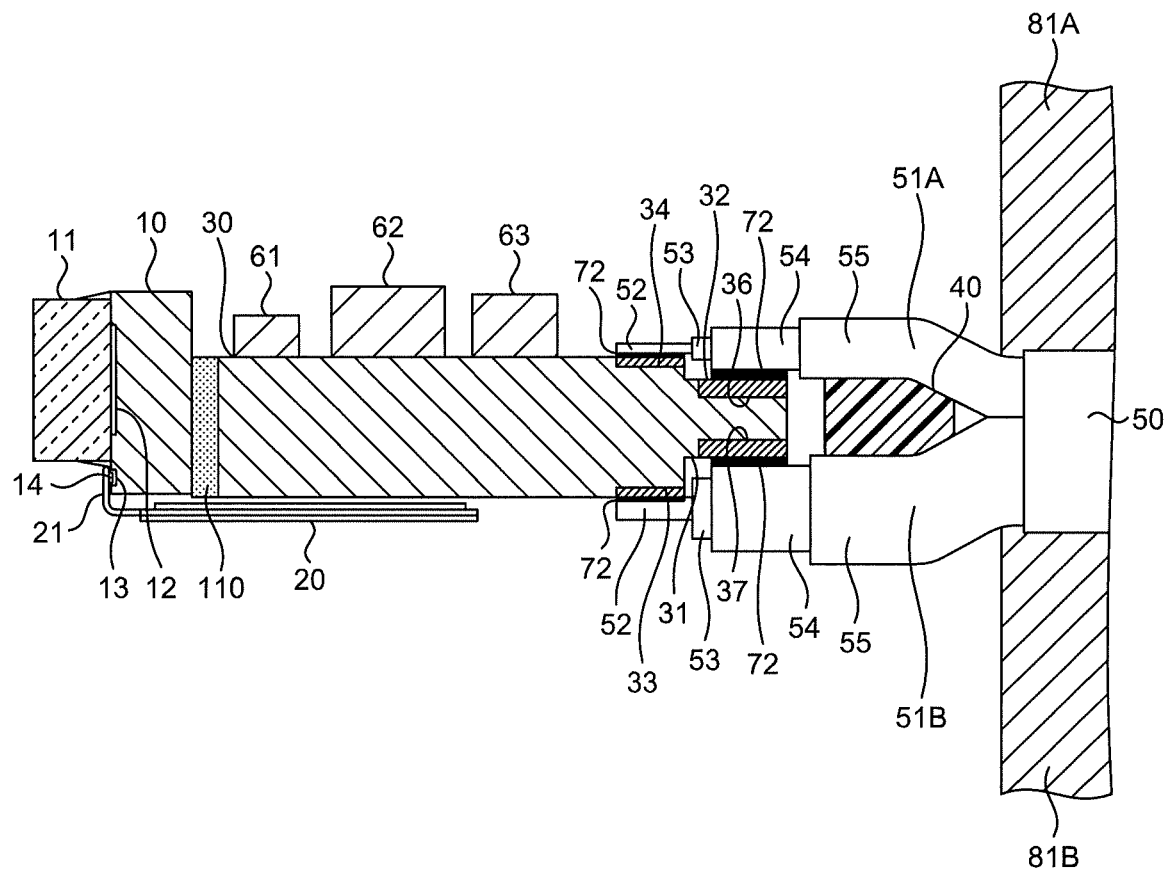
FIG. 8 is a diagram illustrating the process of manufacturing an imaging device according to the first embodiment.

After the cores 52 and 56 are joined to the core joint electrodes 33 and 34 (step S4), as illustrated in FIG. 8, the first grip members 80A and 80B are detached (step S5). In that state, the spacer 40 is being interposed and fixed between the simple cable 56 and the coaxial cables 51A and the coaxial cables 51B.

Figure 9:
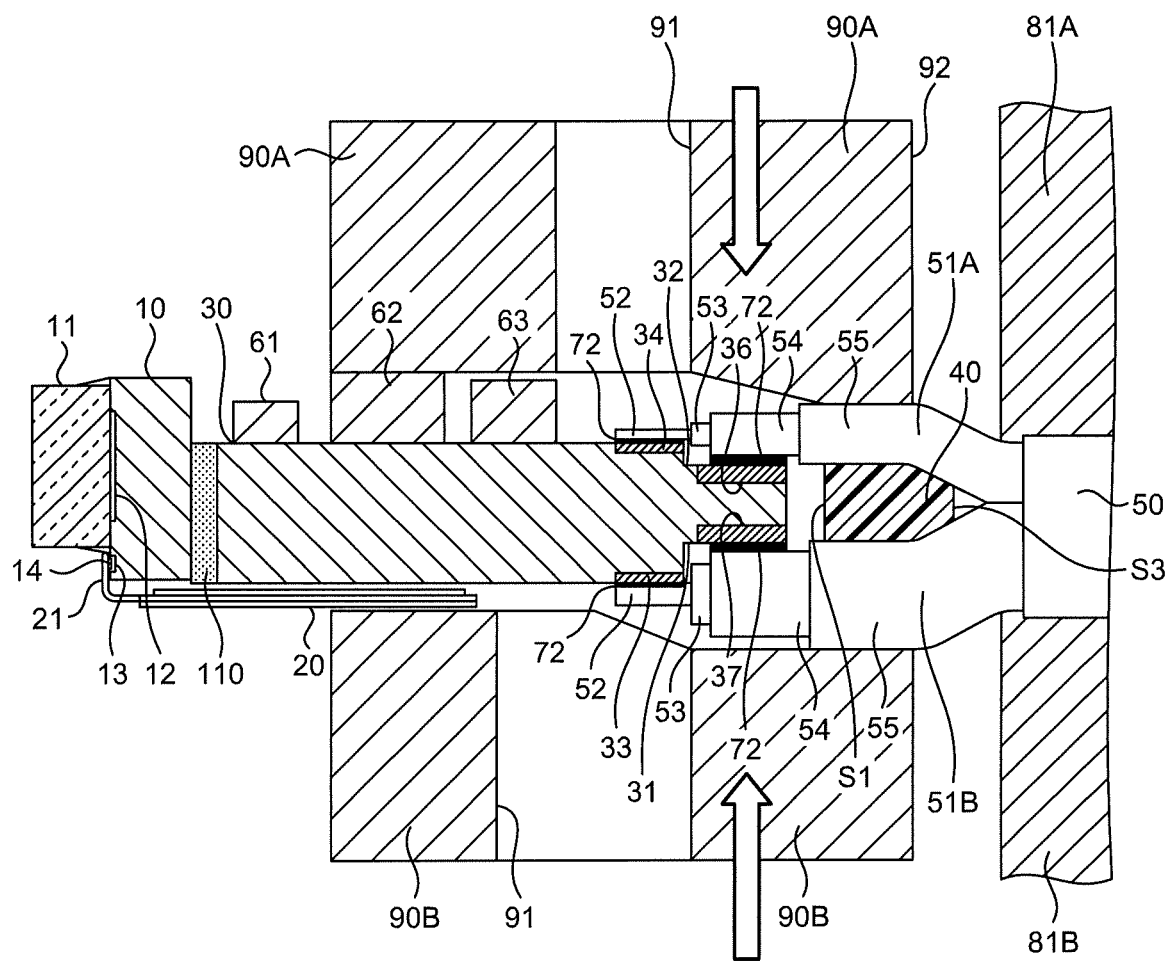
FIG. 9 is a diagram illustrating the process of manufacturing an imaging device according to the first embodiment.

Thereafter, as illustrated in FIG. 9, mold members 90A and 90B are arranged such that the mold members 90A and 90B overlap the mounting board 30, the simple cable 56 and the coaxial cables 51A and 51b from the outer side and are joined and the mold members 90A and 90B are then pressurized and fixed (step S6). The mold members 90A and 90B have a sprue 91 into which a sealing resin is poured. The mold members 90A and 90B are designed such that the mold members 90A and 90B contact the outermost contour of the mounting board 30 on which the electronic components 61, 62 and 6 are mounted and the outer insulators 55 of the coaxial cables 51A and 51B. This makes it possible to cover the joint between the mounting board 30 and the cable with the resin seal 70 and reduce the diameter of the imaging device 100. Furthermore, a surface 92 of the mold members 90A and 90B on the proximal end side is designed such that the surface 92 is positioned on the side of the mounting board 30 with respect to the surface S3 of the spacer 40 on the proximal end side.

Figure 10:
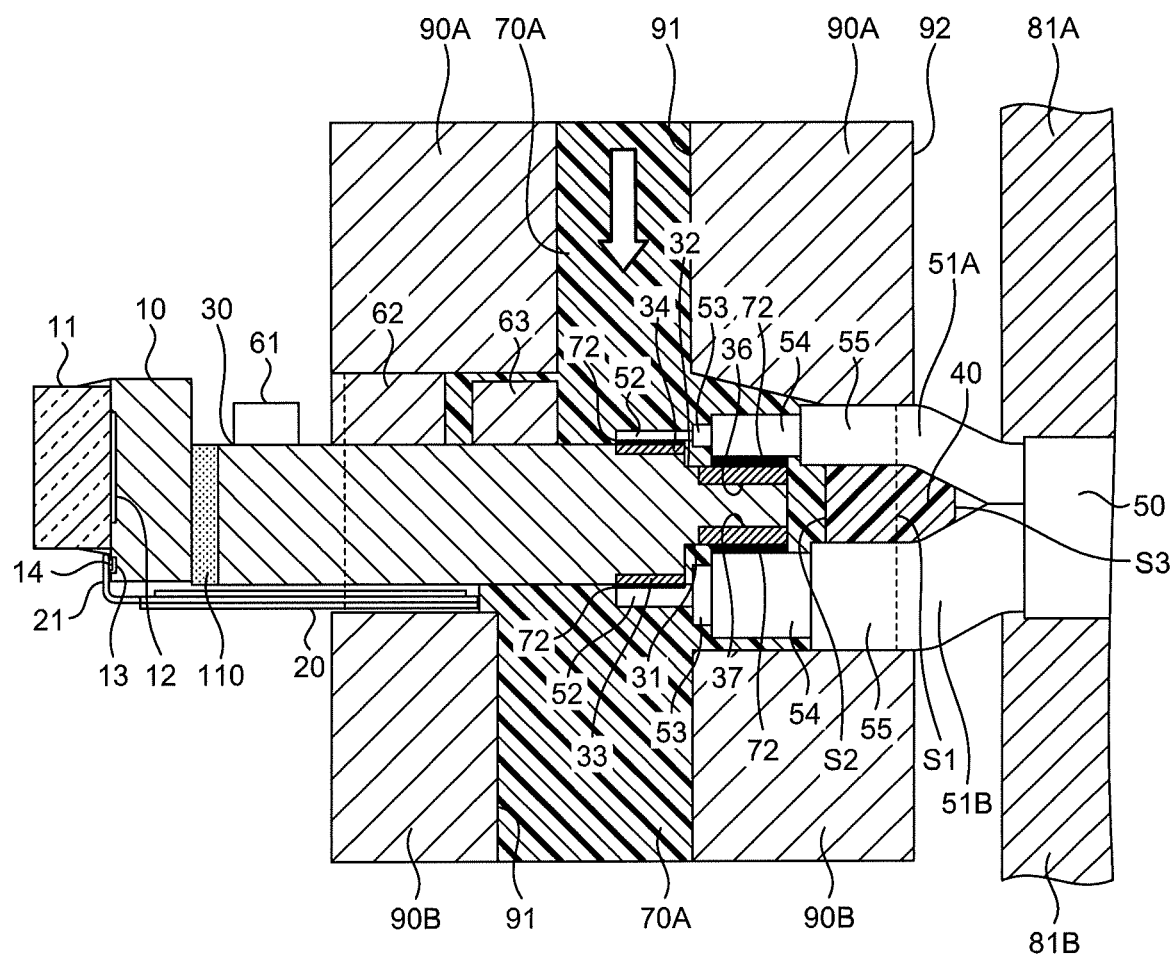
FIG. 10 is a diagram illustrating the process of manufacturing an imaging device according to the first embodiment.

After the mold members 90A and 90B are arranged (step S6), as illustrated in FIG. 10, a sealing resin 70A that is liquid is poured into the sprue 91 of the mold members 90A and 90B (step S7). The sealing resin 70A is extruded into the sprue 91 using a dispenser, or the like. The surface 92 of the mold members 90A and 90B is positioned on the side of the mounting board 30 with respect to the surface S3 of the spacer 40 on the proximal end side and accordingly a position S1 of filling with the liquid sealing resin 70A on the proximal end side (after curing, serving as the surface S1 of the resin seal 70 on the proximal end side) is on the side of the mounting board 30 with respect to the surface S3 of the spacer 40 on the proximal end side.

After filling with the sealing resin 70A (step S7), the sealing resin 70A is cured by being left at normal temperature, heated, or being exposed to ultraviolet light (step S8). When the sealing resin 70A is cured by being exposed to ultraviolet light, the mold members 90A and 90B are made of a material that transmits light. In the first embodiment, is possible to control the shape of the resin seal 70 by filling and sealing the area around the mounting board 30, the simple cable 56, and the coaxial cables 51A and 51B with the sealing resin 70A such that the sealing resin 70A is in a given shape using the mold members 90A and 90B. The spacer 40 is interposed between the simple cable 56 and the coaxial cables 51A and the coaxial cables 51B, which makes it possible to prevent the sealing resin 70A from entering the space between the cables that are divided into two groups and thus reduce the length of the rigid part of the imaging device 100. In the first embodiment, mold members in a size to seal the electronic components 62 and 63 on the mounting board 30 are used as the mold members 90A and 90B. Alternatively, mold members in a size to seal the electronic component 61 may be used.

Figure 11:
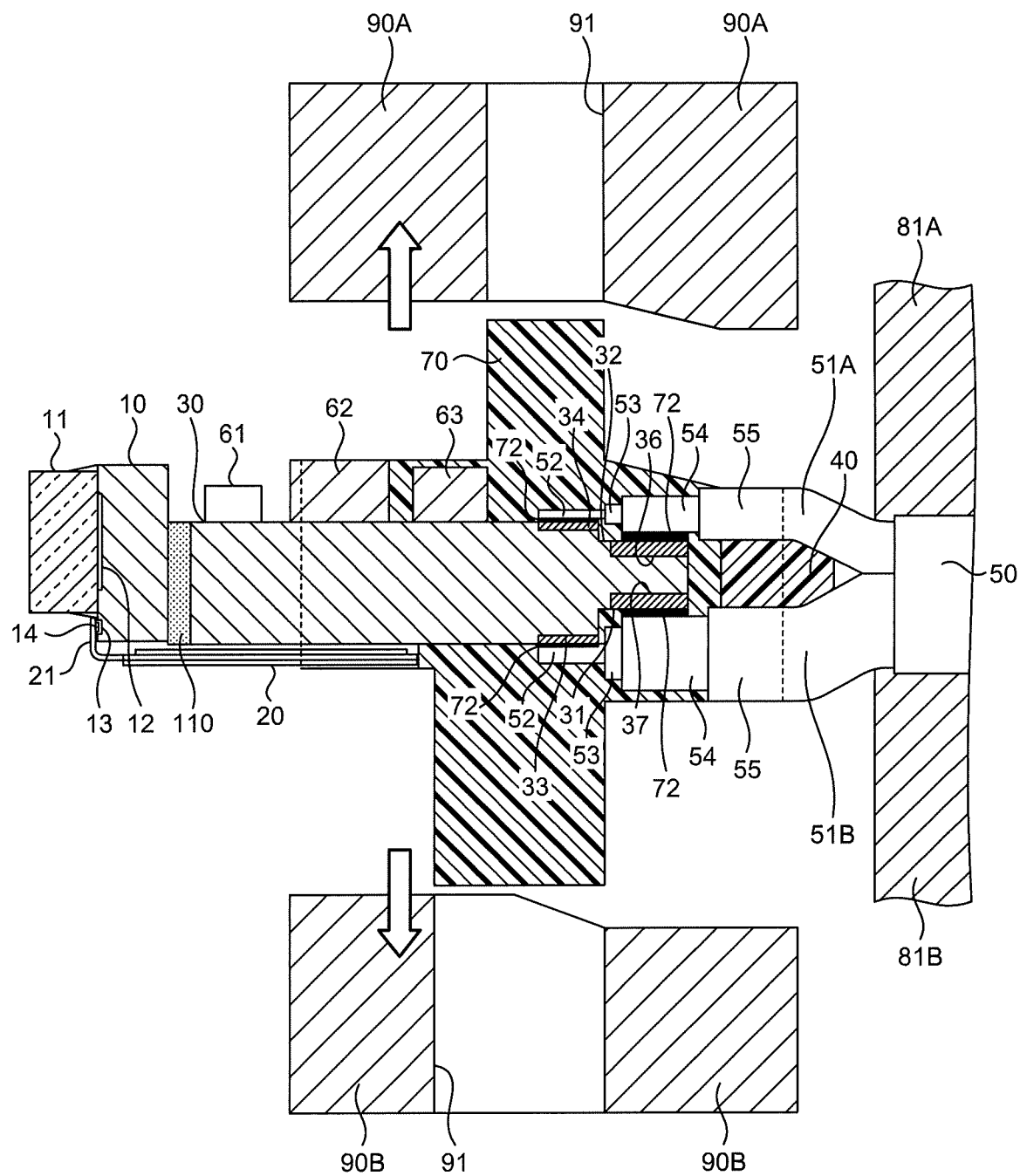
FIG. 11 is a diagram illustrating the process of manufacturing an imaging device according to the first embodiment.

After curing the sealing resin 70A (step S8), as illustrated in FIG. 11, the mold members 90A and 90B are detached (step S9) and an extra part of the cured resin seal 70 is cut or grounded and removed with a tool, or the like (step S10) so that the imaging device 100 illustrated in FIG. 2 can be manufactured.

Figure 12:
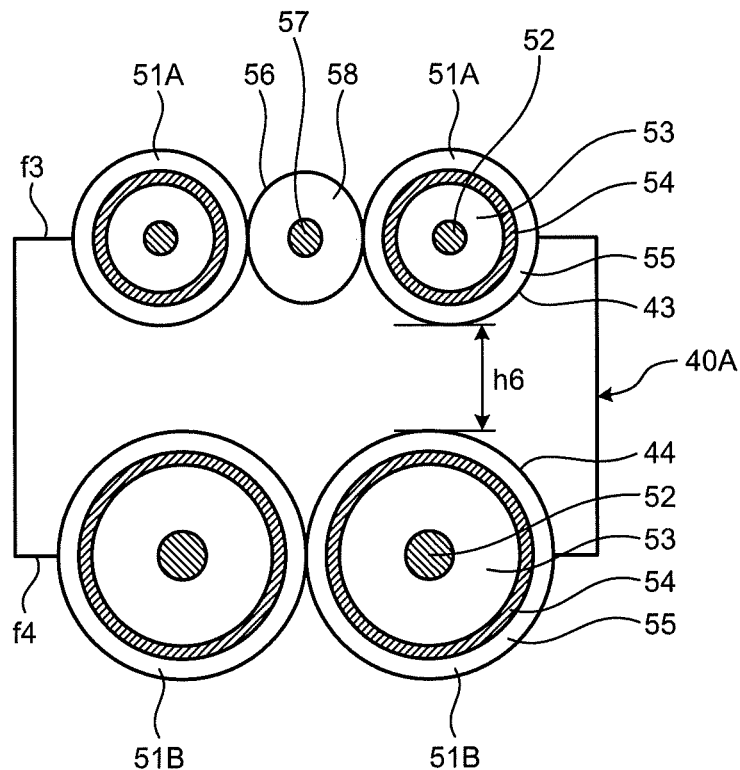
FIG. 12 is a transverse cross-sectional view of a spacer according to Modification 1 of the first embodiment.

In the above-described first embodiment, in the spacer 40, the upper surface f3 and the lower surface f4 of the cable arrangement part 41 are flat; however, grooves in which the cables are arrayed may be provided in the upper surface f3 and the lower surface f4. FIG. 12 is a transverse cross-sectional view of a spacer 40A according to Modification 1 of the first embodiment.

As illustrated in FIG. 12, in the spacer 40A, a groove 43 in which the simple cable 56 and the coaxial cables 51A are arrayed is formed in the upper surface f3 and a groove 44 in which the coaxial cables 51B are arrayed is formed in the lower surface f4. Having the grooves 43 and 44 makes it possible to improve accuracy of positions in which the cables are arrayed. This also makes it possible to prevent the sealing resin 70A from entering not only the space between the cables on the upper side and the lower side but also the space between the simple cable 56 and the coaxial cable 51A that are arranged on the upper side and the space between the coaxial cables 51B. Setting a height h6 from the bottom surface of the groove 43 to the bottom surface of the groove 44 substantially equal to the thickness of the mounting board 30 on the proximal end side makes it possible to easily join the cable to the mounting board 30. The height h6 from the bottom surface of the groove 43 of the spacer 40A to the bottom surface of the groove 44 that is substantially equal to the thickness h1 of the mounting board 30 on the proximal end side means that the height h6 is equal to or larger than a value obtained by subtracting the thickness of the outer insulator 55 from the height h1 and is equal to or smaller than the height h1.

Figure 13:
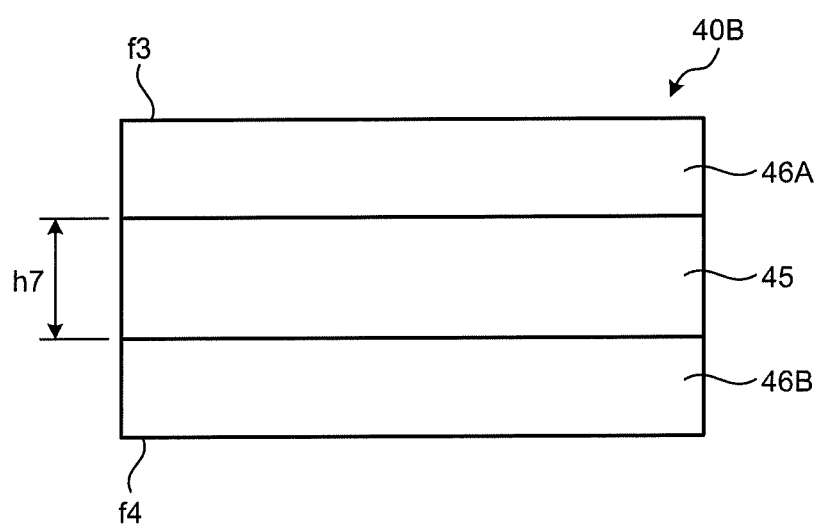
FIG. 13 is a front view of a spacer according to Modification 2 of the first embodiment.

In the above-described first embodiment, the spacer 40 is formed by shaping the homogeneous resin material; however the spacer 40 may be formed using materials that are different from one another. FIG. 13 is a front view of a spacer 40B (of the proximal end side viewed from the imaging element 10) according to Modification 2 of the first embodiment.

The spacer 40B includes a plate-like rigid part 45, a first flexible part 46A that is deposited on the upper surface of the rigid part 45, and a second flexible part 46B that is deposited on the lower surface of the rigid part 45.

The first flexible part 46A and the second flexible part 46B are formed of a material that is softer than the outer coat 58 of the simple cable 56 and the outer insulators 55 of the coaxial cables 51A and 51B. Thus, when the simple cable 56 and the coaxial cables 51A and 51B are arranged on the upper surface f3 and the lower surface f4 of the spacer 40B and the cables are pressurized and fixed with the first grip members 80A and 80B, the first flexible part 46A and the second flexible part 46B are compressed. The first flexible part 46A and the second flexible part 46B form the upper surface f3 and the lower surface f4 of the spacer 40B, which makes it possible to array the simple cable 56 and the coaxial cables 51A and 51B stably. This also makes it possible to prevent the sealing resin from entering not only the space between the cables on the upper side and the lower side but also the space between the simple cable 56 and the coaxial cable 51A that are arranged on the upper side and the space between the coaxial cables 51B. Setting a height h7 of the rigid part 45 substantially equal to the thickness h1 of the mounting board 30 on the proximal end side makes it possible to easily join the cable to the mounting board 30. The height h7 of the rigid part 45 of the spacer 40B substantially equal to the thickness h1 of the mounting board 30 on the proximal end side means that the height h7 is equal to or larger than a value obtained by subtracting the thickness of the outer insulator 55 from h1 and is equal to or smaller than h1.

Figure 14:
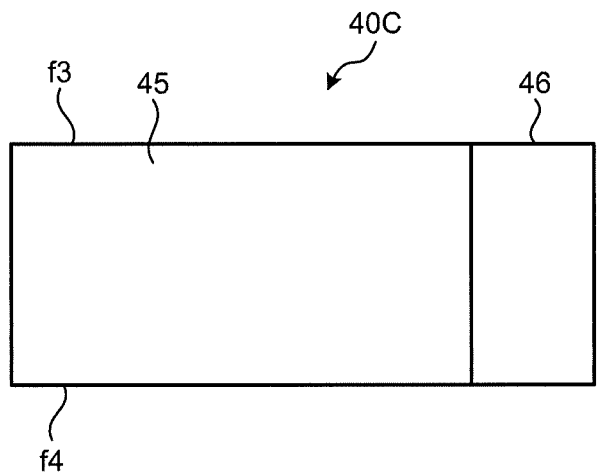
FIG. 14 is a side view of a spacer according to Modification 3 of the first embodiment.

In the above-described first embodiment, the spacer 40 includes the rectangular cable arrangement part 41 and the tapered slope 42; however, the spacer 40 is not limited to these shapes, and a spacer formed of only the cable arrangement part 41 may be used. A spacer whose initial shape forms a rectangle but, when cables are arrayed, forms a slope because the proximal end side is compressed may be used. FIG. 14 is a side view of a spacer 40C according to Modification 3 of the first embodiment.

The spacer 40C includes the rigid part 45 on the side of the mounting board 30 and a flexible part 46 on the proximal end side (on the side of the clustered cable 50). The flexible part 46 is formed of a material that is softer than the outer coat 58 of the simple cable 56 and the outer insulators 55 of the coaxial cables 51A and 51B. Thus, when the simple cable 56 and the coaxial cables 51A and 51B are arranged on the upper surface f3 and the lower surface f4 of the spacer 40C and the cables are pressurized and fixed with the first grip members 80A and 80B, the flexible part 46 is compressed and accordingly a slope is formed.

Figure 15:
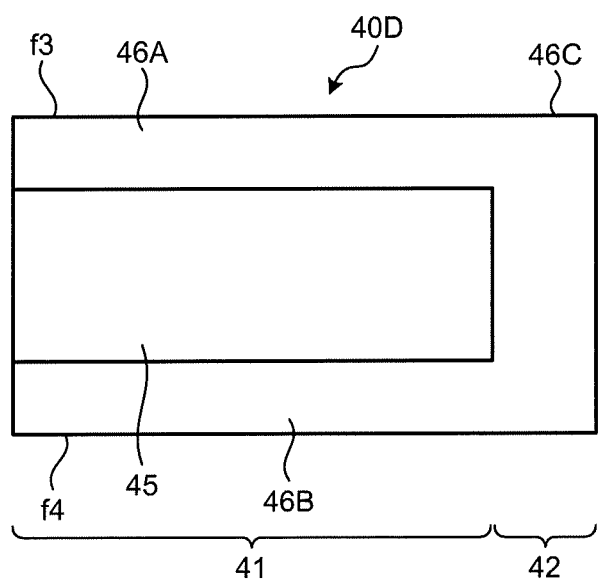
FIG. 15 is a side view of a spacer according to Modification 4 of the first embodiment.

The spacer 40 may be a combination of Modifications 2 and 3 described above. FIG. 15 is a side view of a spacer 40D according to Modification 4 of the first embodiment.

The spacer 40D includes the cable arrangement part 41 formed of the first flexible part 46A, the rigid part 45 and the second flexible part 46B; and the slope 42 that is formed of a third flexible part 46C. The first flexible part 46A, the second flexible part 46B and the third flexible part 46C are formed of a material that is softer than the outer coat 58 of the simple cable 56 and the outer insulators 55 of the coaxial cables 51A and 51B. For this reason, when the simple cable 56 and the coaxial cables 51A and 51B are arranged on the upper surface f3 and the lower surface f4 of the spacer 40D and the cables are pressurized and fixed with the first grip members 80A and 80B, the first flexible part 46A and the second flexible part 46B are compressed. The first flexible part 46A and the second flexible part 46B form the upper surface f3 and the lower surface f4 of the spacer 40D, which makes it possible to array the simple cable 56 and the coaxial cables 51A and 51B stably. Furthermore, when the third flexible part 46C is pressurized and fixed with the first grip members 80A and 80B, the third flexible part 46C is compressed and accordingly forms a slope.

Second Embodiment

Figure 16:
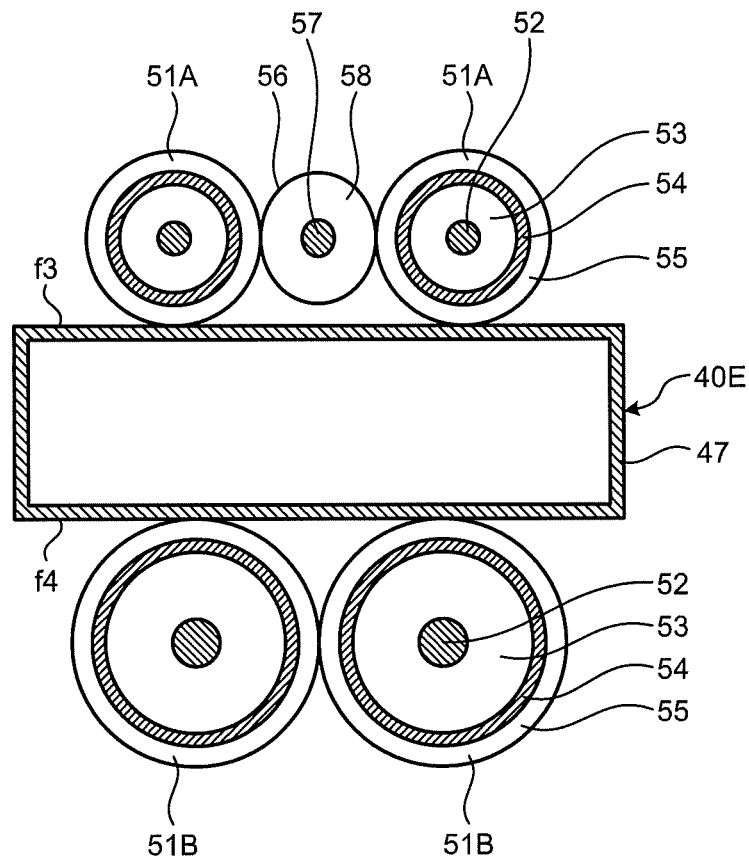
FIG. 16 is a longitudinal cross-sectional view of a spacer according to a second embodiment.
Figure 17:
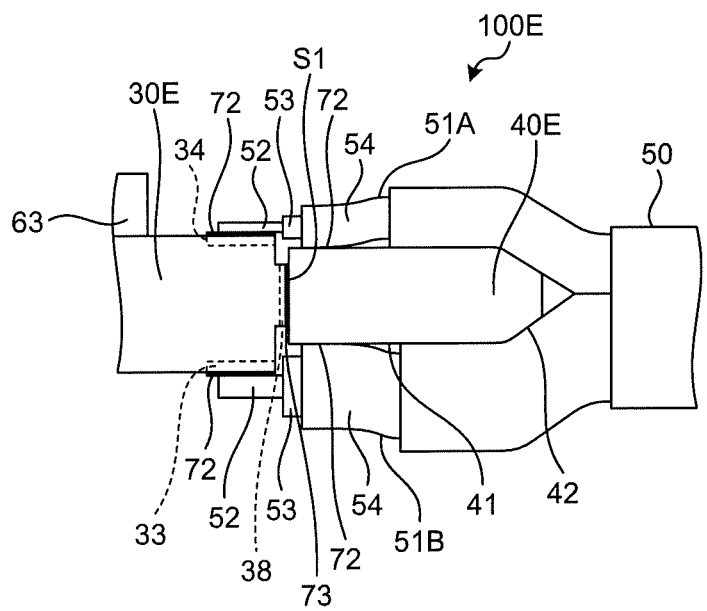
FIG. 17 is a partial side view of an imaging device using the spacer in FIG. 16.

A ground pattern may be formed on the surface of the spacer 40. FIG. 16 is a transverse longitudinal cross-sectional view of a spacer 40E according to a second embodiment. FIG. 17 is a partial side view of an imaging device 100E using the spacer 40E in FIG. 16.

The spacer 40E includes the cable arrangement part 41 in which the distance between the upper surface f3 and the lower surface f4 is uniform, that is, that is rectangular in a cross-sectional view taken along the A-A line; and the slope 42 that is tapered, and a ground pattern 47 is formed over the surface of the spacer 40E. The shield cables 54 of the coaxial cables 51A and 51B are joined to the ground pattern 47 via the solder 72. The spacer 40E arrays the cables and prevents the sealing resin from entering the space between cables and also functions as a shield joint electrode.

In the proximal end of a mounting board 30E, an outer joint electrode 38 is formed instead of the shield cable joint electrodes 36 and 37 and is joined to the ground pattern 47 of the spacer 40E using an anisotropic conductive material 73. Soldering may be used for the joining without the anisotropic conductive material 73. On the mounting board 30E, only the core joint electrodes 33 and 34 to which the cores 52 and 57 are joined are formed and the core 57 of the simple cable 56 and the shield cables 54 of the coaxial cables 51A and 51B are joined using the solder 72.

In the second embodiment, as in the first embodiment, arranging the spacer 40E between cables makes it possible to inhibit the sealing resin from entering the space between cables and thus prevent an increase in rigid length and forming the ground pattern 47 over the surface of the spacer 40E makes it possible to improve transmission quality.

Third Embodiment

Figure 18:
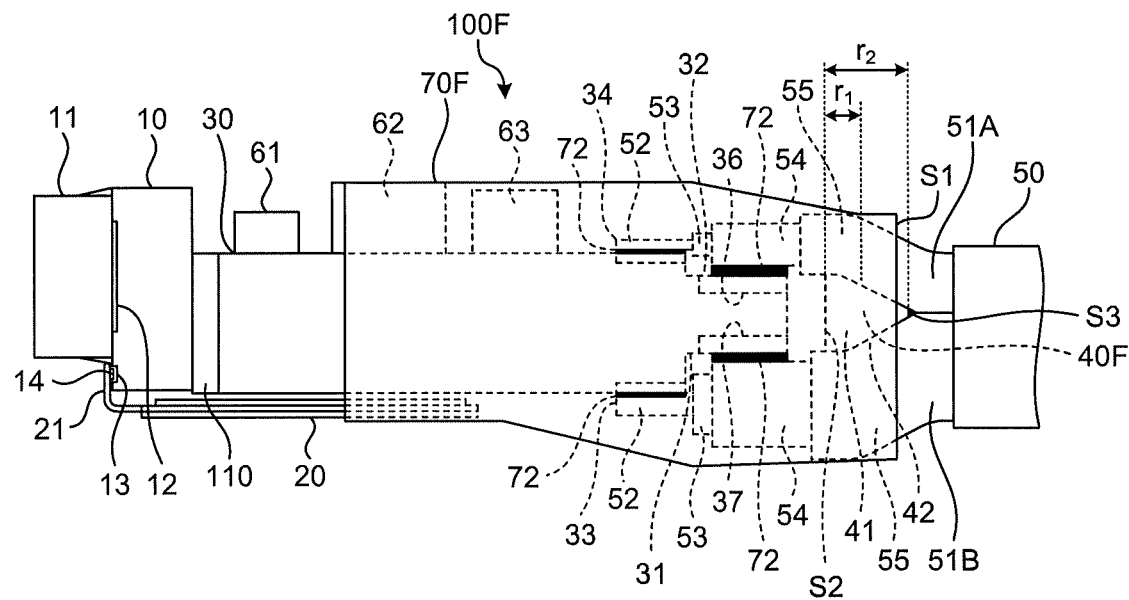
FIG. 18 is a side view of an imaging device according to a third embodiment.

In the imaging device 100 of the first embodiment, the surface S1 of the resin seal 70 on the proximal end side is positioned on the cable arrangement part 41 of the spacer 40. Alternatively, the length r1 of the cable arrangement part 41 in the direction of optical axis may be shortened such that the surface S1 of the resin seal 70 on the proximal end side is positioned on the slope 42. FIG. 18 is a side view of an imaging device 100F according to a third embodiment.

As illustrated in FIG. 18, in the imaging device 100F, the surface S1 of a resin seal 70F on the proximal end side is positioned on the slope 42 of a spacer 40F. The length r1 of the cable arrangement part 41 of the spacer 40F is shorter than the length r1 of the cable arrangement part 41 of the spacer 40 of the first embodiment in the direction of optical axis and a length r2 of the spacer 40F in the direction of optical axis is shorter than the length r2 of the spacer 40 of the first embodiment in the direction of optical axis.

The surface S1 of the resin seal 70F on the proximal end side is positioned on the side of the clustered cable 50 with respect to the surface S2 of the spacer 40F on the side of the mounting board 30 and is positioned on the side of the mounting board 30 with respect to the surface S3 of the spacer 40F on the proximal end side, which makes it possible to prevent the sealing resin from entering the space between cables. The rigid part extends to the surface S3 of the spacer 40F on the proximal end side and using the spacer 40F whose length r2 in the direction of optical axis is short makes it possible to shorten the hard length of the imaging device 100F.

Fourth Embodiment

Figure 19:
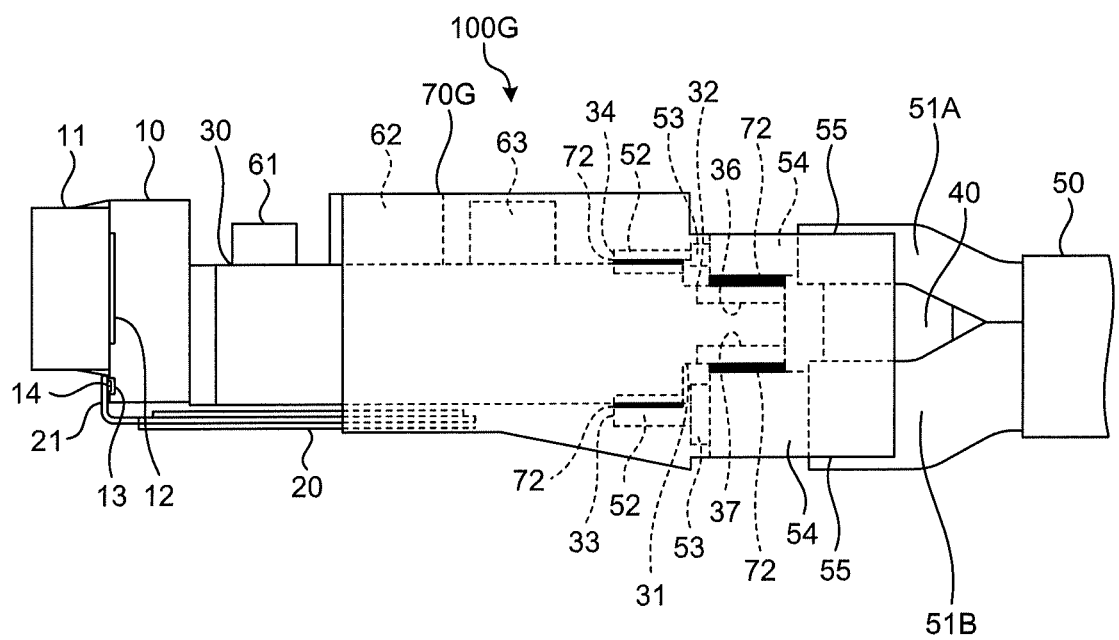
FIG. 19 is a side view of an imaging device according to a fourth embodiment.

In the first to third embodiments, the resin seal 70 seals the electronic components 62 and 63, the simple cable 56, and the outer insulators 55 of the coaxial cables 51A and 51B. It suffices if the shield cables 54 of the coaxial cables 51A and 51B are sealed, and the outer circumferences of the coaxial cables 51A and 51B with respect to the shield cables 54 need not be sealed. FIG. 19 is a side view of an imaging device 100G according to a fourth embodiment.

As illustrated in FIG. 19, in the imaging device 100G, a resin seal 70G seals the electronic components 62 and 63, the overall simple cable 56, and the space of width to the outermost surfaces of the shield cables 54 of the coaxial cables 51A and 51B. This increases the space around the outer circumferences of the cables and, when the imaging device 100G is used as an endoscope, the space is usable for other channels and members.

In the cable mounting structure and the endoscope according to the disclosure, the spacer is arranged between at least two cables and thus the sealing resin does not enter the proximal end side of the clustered cable with respect to the spacer, which makes it possible to keep the length of the rigid part uniform, and the spacer and the sealing resin makes it possible to prevent steam from entering and thus reduce effect on electronic components in autoclave sterilization.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A cable mounting structure comprising:
   a clustered cable including at least two cables covered with an integration coat;
   a spacer configured to divide the at least two cables that are exposed by removing the integration coat at one end of the clustered cable into two groups and array the two groups of the cables along a upper surface and a lower surface of the spacer;
   a mounting board including a upper-side cable joint electrode to which a cable arrayed on the upper surface of the spacer is joined and a lower-side cable joint electrode to which a cable arrayed on the lower surface of the spacer is joined; and
   a resin seal in which a joint between the mounting board and the at least two cables and a mounting board side of the spacer is covered and sealed with a sealing resin,
   wherein an end face of the resin seal on a side of the clustered cable is positioned on a side of the mounting board with respect to an end of the spacer on a side of the clustered cable.

2. The cable mounting structure according to claim 1, wherein the spacer includes grooves in the upper surface and the lower surface in which the at least two cables are arrayed.

3. The cable mounting structure according to claim 1, wherein the spacer includes
   a plate rigid part,
   a first flexible part that is deposited on a upper surface of the rigid part, and
   a second flexible part that is deposited on a lower surface of the rigid part.

4. The cable mounting structure according to claim 1, wherein the spacer includes
   a cable arrangement part in which a distance between an upper surface and a lower surface of the cable arrangement part is uniform and that is arranged on a side of the mounting board, and
   a slope that has a tapered shape in which a distance between an upper surface and a lower surface of the slope gradually reduces from a side of the mounting board toward a side of the clustered cable and that is formed integrally with the cable arrangement part on a clustered cable side of the cable arrangement part.

5. The cable mounting structure according to claim 1, wherein
   the clustered cable includes coaxial cores each including a core that is a conductor, an inner insulator configured to cover the core, a shield cable that is formed around the inner insulator, and an outer insulator configured to cover the shield cable,
   the mounting board includes steps each of which is concave with respect to a reference surface in each of the upper surface and the lower surface of the mounting board,
   shield cable joint electrodes are formed on the steps in the upper surface and the lower surface, respectively, each shield cable being joined to each shield cable joint electrode, and
   core joint electrodes each is formed on the reference surface, each core being joined to each core joint electrode.

6. The cable mounting structure according to claim 1, wherein
   the clustered cable includes coaxial cores each including a core that is a conductor, an inner insulator configured to cover the core, a shield cable that is formed around the inner insulator, and an outer insulator configured to cover the shield cable,
   a ground pattern to which the shield cable is joined is formed on an outer circumferential surface of the spacer, and
   in the mounting board, a core joint electrode to which the core is joined is formed on at least any one of the upper surface and the lower surface of the mounting board and an outer joint electrode that is joined to the ground pattern is formed on an end face of the mounting board on a side of the clustered cable.

7. The cable mounting structure according to claim 1, wherein a height of the spacer from the upper surface to the lower surface of the spacer on a side of the mounting board is substantially equal to a thickness of the mounting board on a proximal end side.

8. An endoscope comprising
   an insertion portion provided with an imaging device at a distal end of the insertion portion, the imaging device including:
   an imaging element configured to generate an electric signal by receiving light and performing photoelectric conversion on the light; and
   the cable mounting structure according to claim 1, the imaging device being configured to perform image processing on the electric signal that is generated by the imaging element using the mounting board of the cable mounting structure.

* * * * *